(12) United States Patent
Brunneke

(10) Patent No.: US 7,452,155 B2
(45) Date of Patent: Nov. 18, 2008

(54) BALL AND SOCKET JOINT

(75) Inventor: Hans-Gerd Brunneke, Osnabrück (DE)

(73) Assignee: ZF Lemförder Metallwaren AG, Stemwede-Dielingen (DE)

( * ) Notice: Subject to any disclaimer, the term of this patent is extended or adjusted under 35 U.S.C. 154(b) by 576 days.

(21) Appl. No.: 11/121,865

(22) Filed: May 4, 2005

(65) Prior Publication Data
US 2005/0207830 A1    Sep. 22, 2005

Related U.S. Application Data

(63) Continuation of application No. PCT/DE2004/000384, filed on Feb. 27, 2004.

(30) Foreign Application Priority Data

Feb. 27, 2003    (DE) .................................. 103 08 809

(51) Int. Cl.
F16C 11/06    (2006.01)
(52) U.S. Cl. .................. 403/135; 403/27; 403/122
(58) Field of Classification Search ............... 403/27, 403/122, 135; 384/277, 448; 340/454, 686.1, 340/686.2
See application file for complete search history.

(56) References Cited

U.S. PATENT DOCUMENTS 3,102,759 A * 9/1963 Stewart ....................... 384/276
3,602,560 A * 8/1971 Memmel ..................... 403/140
5,701,119 A * 12/1997 Jurras, III .................... 340/682
6,366,201 B1 * 4/2002 Hanisko ................ 188/1.11 W
6,773,197 B2 * 8/2004 Urbach ........................ 403/135

FOREIGN PATENT DOCUMENTS

| DE | 195 46 084 |  | 5/1997 |
| DE | 100 09 054 |  | 9/2001 |
| DE | 10140683 | A1 * | 3/2003 |
| FR | 2833321 | A1 * | 6/2003 |
| JP | 56 006911 |  | 1/1981 |

* cited by examiner

Primary Examiner—Daniel P. Stodola
Assistant Examiner—Ernesto Garcia
(74) Attorney, Agent, or Firm—McGlew & Tuttle, P.C.

(57) ABSTRACT

A ball and socket joint for a motor vehicle, especially for the chassis of the motor vehicle, has a ball and socket joint housing (1), which has a joint opening and in which a bearing shell (5) made of an insulating material is arranged. A ball pivot (4), which is made of an electrically conductive material, has a joint ball (2) and a pivot (3), and which is mounted with its joint ball (2) rotatably and pivotably in the bearing shell (5) and projects from the ball and socket joint housing with its pivot (3) through the opening of the joint. An electrode (14) is arranged in the wall of the bearing shell (5) at a distance (Δ) from the joint ball (2), and the electrode (14) and the joint ball (2) are electrically insulated against each other via the bearing shell (5). Furthermore, between the joint ball (2) and the ball and socket joint housing (1), the wall has at least two layers (12, 13) arranged one after another, between which the electrode (14) is arranged.

3 Claims, 2 Drawing Sheets

BALL AND SOCKET JOINT

CROSS REFERENCE TO RELATED APPLICATION

This is a continuation of and claims the benefit (35 U.S.C. §120 and 365(c)) of copending International Application PCT/DE 2004/000384 of Feb. 27, 2004, which designated inter alia the United States and which claims the priority of German Application DE 103 08 809.1 of Feb. 27, 2003. The entire contents of each application is hereby incorporated by reference in its entirety.

FIELD OF THE INVENTION

The present invention pertains to a ball and socket joint for a motor vehicle, especially for the chassis of a motor vehicle with a ball and socket joint having a joint opening, in which housing a bearing shell made of an insulating material is arranged, and with a ball pivot, which is made of an electrically conductive material and has a joint ball and a pivot, and which is mounted with its joint ball rotatably and pivotably in the bearing shell and projects with its pivot from the ball and socket joint housing through the opening of the joint.

BACKGROUND OF THE INVENTION

Such a ball and socket joint is described in the German patent application DE 100 09 054, in which the ball and socket joint housing made of an electrically conductive material and the ball pivot are connected via electric lines with an evaluating unit, by means of which excessive wear of the bearing shell, which is characterized by a direct contact between the joint ball and the ball and socket joint housing, can be detected.

DE 195 46 084 C1 discloses a ball and socket joint, e.g., for the suspension of a front wheel of a motor vehicle, in which a ball pivot with a ball head is arranged in a bearing housing through the intermediary of a bearing shell. The ball pivot and the bearing housing are made of a metallic material, whereas the bearing shell is made of a plastic, which does not conduct the electric current. A voltage is applied between the ball pivot and the bearing housing for measuring the wear, and the flowing current is measured.

Furthermore, a ball and socket joint, e.g., for the steering means of a motor vehicle, is known from JP 56006911 A, in which a ball pivot with a joint ball is arranged in a joint housing through the intermediary of a bearing shell. The joint housing is made of a metallic material, whereas the bearing shell is made of an insulating plastic. An electrode made of copper is embedded in the bearing shell, and this electrode does not at first extends to the inner surface of the bearing shell and is not in electric contact with the joint housing, which is connected with a power source via an electric line through the intermediary of a signaling device. When the bearing shell is worn, the electrode comes into direct contact with the joint ball of the ball pivot connected to the ground, whereupon the signaling device is activated.

Greases, which are mixed, for example, with graphite or molybdenum and are thus electrically conductive, are usually used in ball and socket joints for motor vehicles. Furthermore, contaminants, including water, which are likewise conductive, can penetrate into the ball and socket joint. It is thus possible that these substances enter the area between the electrode and the joint ball of, e.g., a ball and socket joint according to JP 56006911 A and form an electric contact resistance there, which has a relatively low resistance because of the short distance between the electrode and the joint ball. However, when an electric current can flow between the electrode and the joint ball, even though the bearing shell does not yet permit a direct contact between the electrode and the joint ball, i.e., the state of wear has not yet developed, this may lead to measuring errors during the determination of the state of wear.

On the other hand, these contaminants may lead to corrosion of the electrode over the lifetime of the above-mentioned ball and socket joint, so that no electric contact or only a weak electric contact will develop in case of wear, i.e., in case of a direct mechanical contact between the electrode and the joint ball. This may also lead to measuring errors during the determination of the state of wear.

SUMMARY OF THE INVENTION

Based on this state of the art, the object of the present invention is to provide a ball and socket joint of the type described in the introduction, in which these measuring errors can be avoided.

The ball and socket joint according to the present invention for a motor vehicle, especially for the chassis of the motor vehicle, has a ball and socket joint housing, which has a joint opening and in which a bearing shell made of an insulating material is arranged, and a ball pivot, which is made of an electrically conductive material and has a joint ball and a pivot, and which is mounted with its joint ball rotatably and pivotably in the bearing shell and projects with its pivot from the ball and socket joint housing through the opening of the joint. An electrode is arranged in the wall of the bearing shell at a distance A from the joint ball, the electrode and the joint ball being electrically insulated from one another via the bearing shell. Furthermore, between the joint ball and the ball and socket joint housing, the wall has at least two layers, which are located one after another and between which the electrode is arranged.

Due to the fact that the electrode is arranged between two layers of the bearing shell, neither grease nor contaminants can come into direct contact with the electrode in the measurement area, so that the drawbacks mentioned in connection with the state of the art are avoided with the ball and socket joint according to the present invention.

The electrode may be made as a metallic film, which is bonded to one of the two layers, for example, during the manufacture of the bearing shell. Furthermore, the electrode can be made of an electrically conductive lacquer, which may be mixed, for example, with electrically conductive particles, such as metal particles.

However, it is also possible to form the electrode as a chemical or galvanic metal plating of one of the two layers, in which case copper proved to be useful for the metal plating of plastics. This metal plating consisting of copper may, furthermore, be provided with a gold or gold alloy coating toward the joint ball, so that the electric transition between the joint ball and the electrode will have the lowest possible contact resistance in case of wear. However, this coating may also be made of other materials with good electric conductivity, e.g., silver or a silver alloy.

The electrode may be designed as a single point electrode, as a planar electrode extending over a larger area or as an array of a plurality of single electrodes electrically connected with one another, the latter two variants making it possible to check a larger area of the bearing shell for wear. The state of wear can be detected only locally with the single point electrode.

Electric contact may develop between the ball pivot and the ball and socket joint housing during a great deflection of the ball pivot. Especially if the electrode is electrically connected with the ball and socket joint housing, this electric contact may misleadingly prompt the evaluating means to determine a state of wear. The ball pivot may therefore be surrounded by a collar made of electrically insulating material in the transition area between the joint ball and the pivot. Besides the electric function, this collar can, however, also act as a mechanical buffer when the ball pivot and the ball and socket joint housing come into contact with one another.

Furthermore, an electric contact can also be established between the ball pivot and the ball and socket joint housing by both the ball and socket joint housing and the ball pivot being directly connected with electrically conductive components, which are in turn electrically in connection with one another. The pivot may be surrounded for this reason by electrically insulating material in an annular pattern at its end area facing away from the joint ball, so that a direct electric contact between the ball pivot and the component fastened to it is prevented from occurring. When the ball pivot is connected with the component by means of a nut made of an electrically conductive material, it is advantageous, furthermore, to provide a washer made of an insulating material between the component and the nut.

The electrode may extend from the wall of the bearing shell to the extent that it is in direct electric contact with the ball and socket joint housing and can be electrically contacted via same. However, a passage is preferably provided in the ball and socket joint housing, through which extends an electric line, which is connected to the electrode and is advantageously electrically insulated against the ball and socket joint housing. If the electrode does not project from the bearing shell, an opening, which extends from the outer side of the bearing shell to the electrode, may likewise be provided in it. The electric line for contacting the electrode can then be introduced into this opening.

If both the electrode and the electric line are electrically insulated against the ball and socket joint housing, it is possible to do away, for example, with the electric insulation of the ball pivot against the ball and socket joint housing or against the component.

Furthermore, a process for manufacturing a bearing shell from an insulating plastic, which has the following process steps:

injection molding of a first layer of the bearing shell,
formation of an electrode on the first layer, and
injection molding of a second layer of the bearing shell on the first layer and the electrode, is provided according to the present invention.

A bearing shell, in which the electrode is an integral part of the bearing shell, is created by the process according to the present invention. As a result, neither grease nor contaminants can come into direct contact with the electrode in the measuring area, so that the drawbacks mentioned in connection with the state of the art are avoided in the bearing shell according to the present invention.

The two layers are located directly at the electrode and directly at each other in areas without electrode, where they can form a connection in substance with one another due to the injection molding.

The electrode may be designed as a metallic foil, which is bonded, for example, onto the first layer. Furthermore, it is possible to apply an electrically conductive lacquer to the first layer to form the electrode.

On the other hand, the electrode may also be formed, however, by the metal plating of at least part of the first layer, especially by a chemical or galvanic process, in which case copper has proved to be a suitable electrode material, besides other materials.

The electrode may be embodied as a single point electrode or as an array of a plurality of single electrodes electrically connected with one another. However, the electrode is preferably designed as a planar electrode extending over a larger area.

To reduce the contact resistance in case of wear, the electrode may be provided with a coating of gold or a gold alloy before the application of the second layer. However, other materials with good electric conductivity, e.g., silver or a silver alloy, may also be used for this coating.

Electrically insulating plastics, such as POM (polyoxymethylene), PEEK (polyether ether ketone) or PA (polyamide), which may additionally also be reinforced with fibers, may be used as materials for the layers of the bearing shell.

The use of the ball and socket joint according to the present invention or of a ball and socket joint provided with a bearing shell manufactured according to the process according to the present invention for wear measurement will be described below.

In the nonworn state, the electrode is electrically insulated against the joint ball by means of the layer of the bearing shell arranged between the electrode and the joint ball. However, movements will occur between the joint ball and the bearing shell due to the operation of the motor vehicle, so that this wall becomes increasingly thinner due to friction and deformation. As a result, the joint ball will have increased clearance in relation to the ball and socket joint housing, until the ball and socket joint becomes unfit for use.

When the layer of the bearing shell located between the electrode and the joint ball is worn to the extent that an electric contact develops between the electrode and the joint ball, this contact can be detected by means of an electric evaluating means. This electric evaluating means can now display the information on the presence of the state of wear to the driver of the vehicle or store it in an electric memory component for reading at a later point in time.

If the state of wear has been detected, the ball and socket joint can be replaced to avoid greater damage.

The degree of wear beginning from which the bearing shell is considered to have been worn off or the clearance of the joint ball in relation to the ball and socket joint housing at which the bearing shell is considered to have been worn off is set by selecting the thickness of the layer of the nonworn bearing shell, which said layer is arranged between the electrode and the joint ball. The closer the electrode to the surface of the bearing shell facing the joint ball, the thinner is the layer that electrically insulates the electrode against the joint ball and the smaller is the wear that will be sufficient to take place until the state of wear is detected.

The evaluating means may have a simple electric circuit with a warning light, a voltage being applied between the ball pivot and the electrode. If there is an electric contact between the electrode and the ball pivot, the warning light lights up to inform the driver of the vehicle of the state of wear. However, if the evaluating means stores the information characterizing the state of wear in a memory, this information can be read, e.g., at preset maintenance intervals. Furthermore, it is possible to connect the evaluating means with an existing onboard computer network or for the evaluating means to form part of this onboard computer network itself.

Using the ball and socket joint according to the present invention or a ball and socket joint manufactured according to the process according to the present invention for a ball and socket joint, it is possible to carry out a permanent monitoring of the wear of the joint in the motor vehicle, so that driving safety is increased. Furthermore, the ball and socket joint according to the present invention has a simple design, so that older vehicles can also be retrofitted with it. Due to the fact that the driver of the vehicle can be informed of the state of wear with simple circuitry means, the complexity of the arrangement is low, so that high reliability can be achieved. Furthermore, monitoring of the state of wear can be embodied at low cost.

The present invention will be described below on the basis of preferred embodiments with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
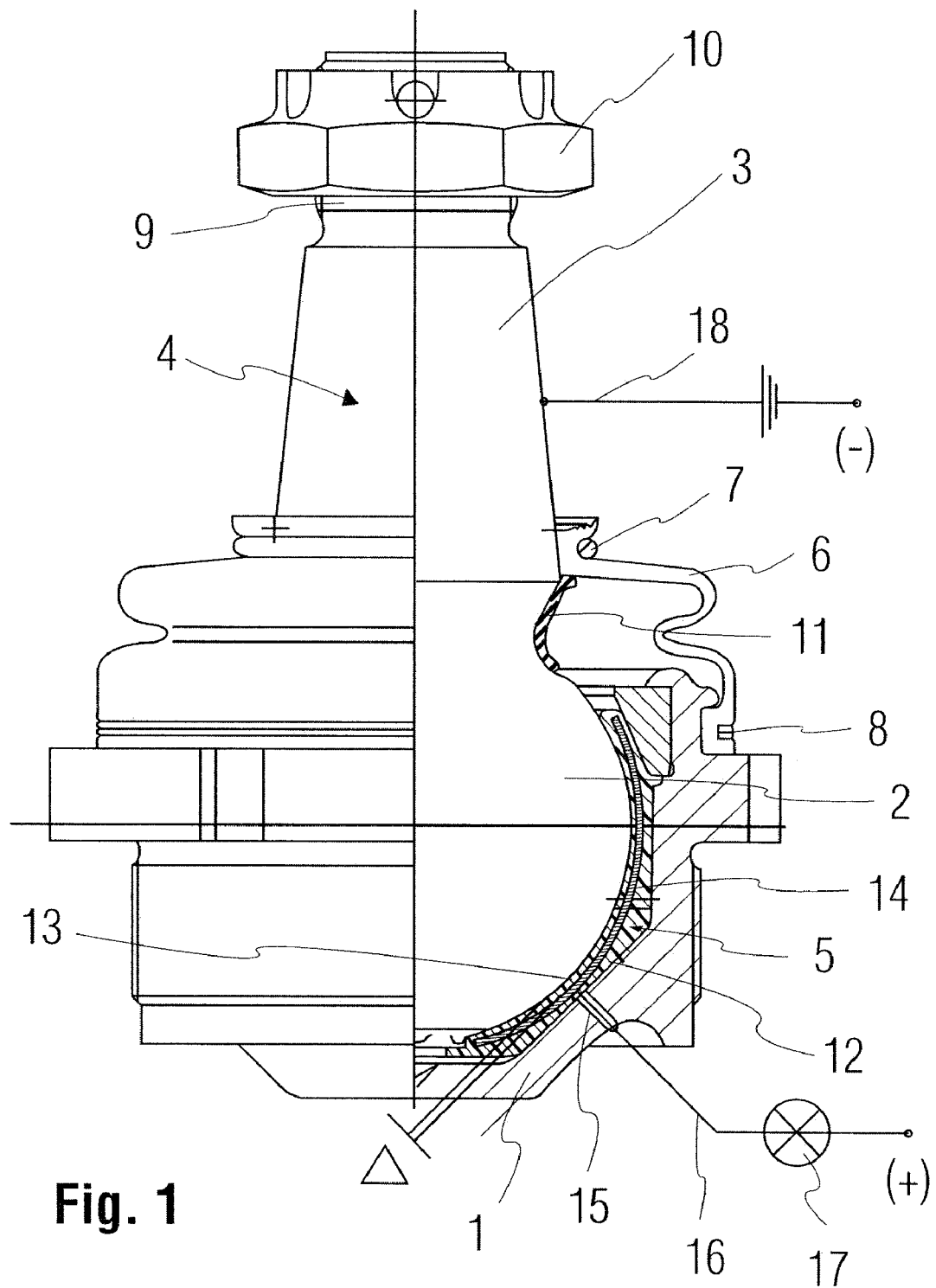
FIG. 1 is a partially cut-away view of a first embodiment of the ball and socket joint according to the present invention.

Referring to the drawings in particular, FIG. 1 shows a partially cut-away view of a first embodiment of the ball and socket joint according to the present invention, in which a ball pivot 4 having a joint ball 2 and a pivot 3 is mounted rotatably and pivotably in a bearing shell 5 in a ball and socket joint housing 1. A sealing bellows 6, which is sealingly in contact with the ball and socket joint housing 1 with one of its ends and with the pivot 3 with its other end and prevents dirt and water from penetrating into the interior of the ball and socket joint housing 1, is arranged between the ball and socket joint housing 1 and the ball pivot 4. In order for this protection to be also maintained during movements of the ball pivot 4 in relation to the ball and socket joint housing 1, the two ends of the sealing bellows 6 are centripetally pretensioned via a straining ring 7 each. At the end area of the pivot 3 facing away from the joint ball 2, a thread 9 with a nut 10 screwed on it is provided to fasten a component. Furthermore, the ball pivot 4 is surrounded by a collar 11 made of an electrically insulating material in the transition area between the joint ball 2 and the pivot 3.

The bearing shell 5 has an outer layer 12 and an inner layer 13, wherein an electrode 14 is arranged between these two layers and is directly in contact with these. The electrode 14 is electrically connected with an incandescent light (or another optical signal transmitter) 17, whose other terminal is connected to the positive pole (+) of a power source, via a first electric line 16 extending through a duct 15 provided in the ball and socket joint housing 1. Both the first electric lime 16 and the electrode 14 are designed here such that they are electrically insulated against the ball and socket joint housing 1.

The ball pivot 4 is connected with its pivot 3 to the negative pole (−) of the power source via a second electric line 18, so that the electrode 14 and the ball pivot 4 are separated from one another electrically only via the inner layer 13 of the thickness Δ. Since this thickness Δ decreases with increasing wear, the maximum allowable wear of the bearing shell 5 can be detected from this thickness.

If the layer 13 is worn and an electric contact becomes established between the ball pivot 4 and the electrode 14, a closed circuit is formed, as a result of which the incandescent light 17 will begin to light up. If the incandescent light 17 is arranged in the interior space of the motor vehicle, the driver of the vehicle can recognize from the lighting of the incandescent light 17 that the bearing shell 5 of the ball and socket joint is worn.

Figure 2:
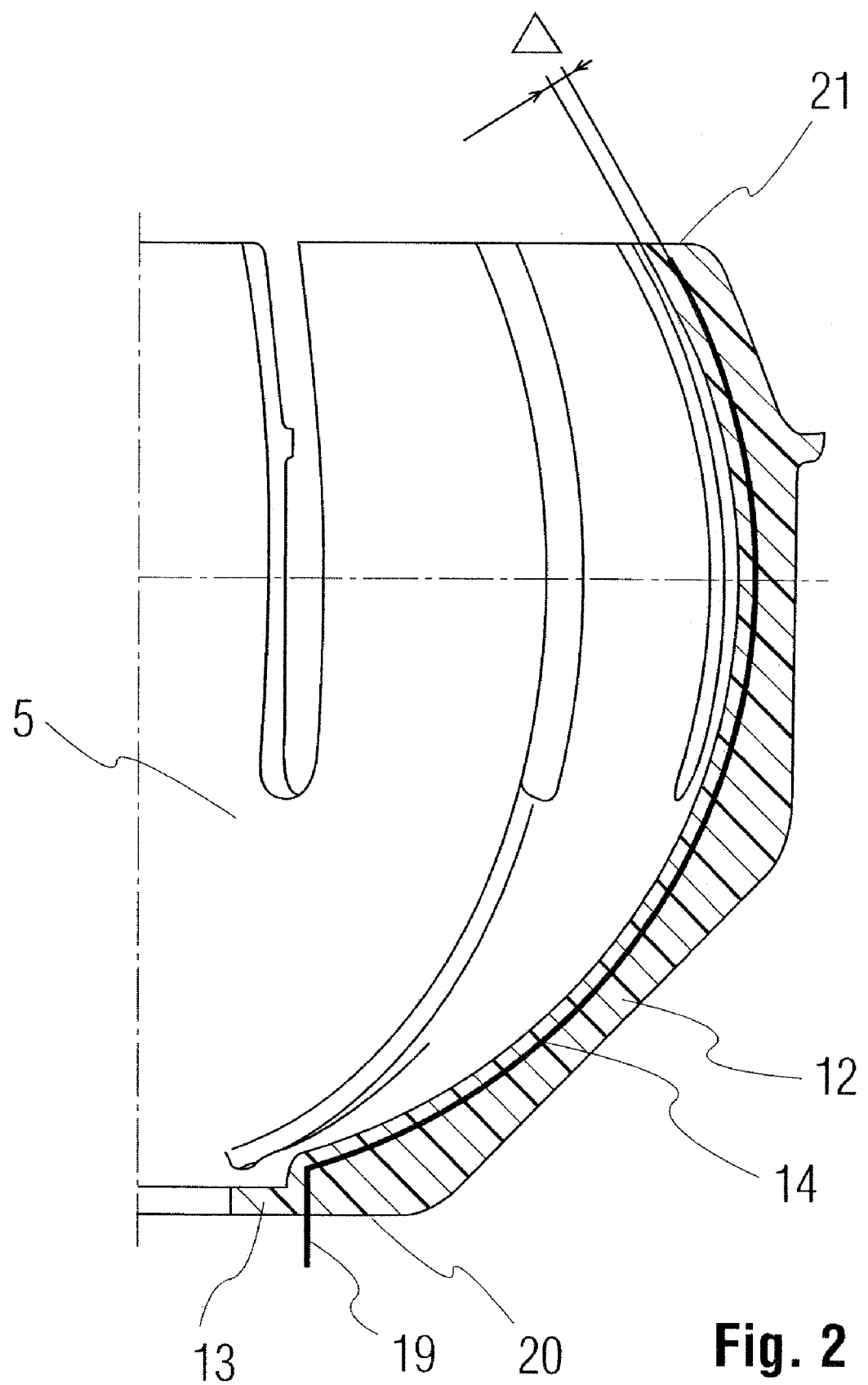
FIG. 2 is a sectional view of part of the bearing shell of the ball and socket joint according to the present invention according to a second embodiment.

FIG. 2 shows a sectional view of a part of a ball and socket joint 50 for a ball and socket joint according to the present invention according to a second embodiment of the present invention. Identical and functionally identical features are designated by the same reference numbers as in the first embodiment. According to the second embodiment, an electrode 14 is arranged in a firmly seated manner in the bearing shell 5 between an outer layer 12 and an inner layer 13, and the electrode 14 is led with one end 19 out of the lower area 20 of the bearing shell 5. In the upper area 21 of the bearing shell 5, the two layers 12 and 13 directly adjoin each other and are connected with one another by a connection in substance.

The end 19 of the electrode 14 may be used, e.g., to establish a direct contact between the electrode 14 and the ball and socket joint housing, via which the electrode 14 can then be electrically contacted. It would be possible in this case to do away with forming a duct for an electric line in the ball and socket joint housing.

While a specific embodiment of the invention has been shown and described in detail to illustrate the application of the principles of the invention, it will be understood that the invention may be embodied otherwise without departing from such principles.

APPENDIX

List of Reference Numbers

1 Ball and socket joint housing
2 Joint ball
3 Pivot
4 Ball pivot
5 Bearing shell
6 Sealing bellows
7 Straining ring
8 Straining ring
9 Thread
10 Nut
11 Collar
12 Outer layer of bearing shell
13 Inner layer of bearing shell
14 Electrode
15 Duct
16 First electric line
17 Incandescent light
18 Second electric line
19 End of electrode led out of the bearing shell
20 Lower area of bearing shell
21 Upper area of bearing shell
Δ Distance

What is claimed is:
1. A ball and socket joint comprising:
a ball and socket joint housing having a joint opening;
a bearing shell made of an insulating material, said bearing shell being arranged in said housing, said bearing shell comprising two layers located one after another;

a ball pivot made of an electrically conductive material, said ball pivot having a joint ball and a pivot, said joint ball being mounted in said bearing shell with said pivot projecting out of said housing through the opening of the joint;

an electrode arranged directly between said two layers in said wall of said bearing shell and disposed at a spaced location from said joint ball, said electrode and said joint ball being electrically insulated against each other via said bearing shell;

a duct extending from said electrode to outside of said bearing shell; and an electrical line provided in said duct and connected to said electrode as a sole electrical connection for said electrode.

2. A ball and socket joint in accordance with claim 1, wherein said electrode comprises a metallic foil.

3. A ball and socket joint in accordance with claim 1, wherein said electrode is made of an electrically conductive lacquer.

* * * * *